(12) United States Patent
Cordingley et al.

(10) Patent No.: US 9,247,739 B2
(45) Date of Patent: Feb. 2, 2016

(54) HERBICIDAL COMPOSITIONS

(75) Inventors: Matthew Robert Cordingley, Bracknell (GB); Andreas Zoschke, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 579 days.

(21) Appl. No.: 12/863,611

(22) PCT Filed: Jul. 21, 2008

(86) PCT No.: PCT/GB2008/002520
§ 371 (c)(1),
(2), (4) Date: Oct. 13, 2010

(87) PCT Pub. No.: WO2009/092986
PCT Pub. Date: Jul. 30, 2009

(65) Prior Publication Data
US 2011/0028324 A1    Feb. 3, 2011

Related U.S. Application Data

(60) Provisional application No. 61/023,444, filed on Jan. 25, 2008.

(51) Int. Cl.
*A01N 37/38* (2006.01)
*A01N 37/42* (2006.01)
*A01N 61/00* (2006.01)

(52) U.S. Cl.
CPC ............. *A01N 37/38* (2013.01); *A01N 37/42* (2013.01); *A01N 61/00* (2013.01)

(58) Field of Classification Search
CPC ........ A01N 37/38; A01N 37/42; A01N 61/00
USPC .......................................... 504/127, 130, 206
See application file for complete search history.

(56) References Cited

U.S. PATENT DOCUMENTS

| | | | |
|---|---|---|---|
| 3,935,000 A | 1/1976 | Fischer | |
| 4,203,253 A | 5/1980 | Broomfield, Jr. et al. | |
| 4,693,745 A * | 9/1987 | Brunner | 504/221 |
| 6,200,929 B1 * | 3/2001 | Horibe et al. | 504/127 |
| 6,727,205 B2 * | 4/2004 | Brinkman | 504/248 |
| 2005/0032648 A1 | 2/2005 | Cooper | |
| 2005/0187108 A1 | 8/2005 | Ng et al. | |

FOREIGN PATENT DOCUMENTS

| | | |
|---|---|---|
| CN | 1233397 | 11/1999 |
| WO | 03084325 | 10/2003 |
| WO | 2007031735 | 3/2007 |

OTHER PUBLICATIONS

Stamm, Gregory, The Effects of Glyphosate/Growth Regulator Combinations on Blackberry Control, 1982, Storrs Agricultural Experiment Station. Paper 22, pp. 1-17.*

McCullough, Patrick, Kentucky Bluegrass Control With Postemergence Herbicides, 2006, HortScience, vol. 41, Issue 1, pp. 255-258.*

* cited by examiner

*Primary Examiner* — Sue Liu
*Assistant Examiner* — Andriae M Holt
(74) *Attorney, Agent, or Firm* — James Cueva

(57) ABSTRACT

The present invention relates to a method of controlling weeds using mixtures of non-selective herbicides and plant growth regulators. It also relates to mixtures of non-selective herbicides and plant growth regulators per se, and compositions comprising the same.

21 Claims, No Drawings

HERBICIDAL COMPOSITIONS

This application is a 371 of International Application No. PCT/GB2008/002520 filed Jul. 21, 2008, which claims priority to U.S. 60/023,444 filed Jan. 25, 2008, the contents of which are incorporated herein by reference.

The present invention relates to a method of controlling weeds using mixtures of non-selective herbicides and compounds regulating growth ("plant growth regulators"). It also relates to mixtures of non-selective herbicides and plant growth regulators per se, and compositions comprising the same.

The protection of crops (from damage due to weeds and other vegetation that inhibit crop growth, reduce quality and/or hinder farming operations) is a constantly recurring problem in agriculture and turf management for professional home and garden use. In addition, aesthetically, it may be of interest to remove such unwanted weeds and vegetation, for example, when growing turf in areas such as golf courses, lawns and public parks. To help combat these problems, researchers in the field of synthetic chemistry have produced an extensive variety of chemicals and chemical formulations effective in the control of such unwanted growth. Chemical herbicides of many types, and having various modes of action, have been disclosed in the literature and a large number are in commercial use. Commercial herbicides and some that are still in development are described in 'The Pesticide Manual', $14^{th}$ Edition, published 2006 by the British Crop Protection Council.

Plant growth regulators are often used to regulate the growth and development of crop plants. For example, plant growth regulators are used to slow the development of a crop (such as oil seed rape) so that it flowers at a desired time, reduce the height of a crop (such as in cereals) so that it is less susceptible to lodging, increase nitrogen efficiency, regulate flowering and fruit set of a crop (such as fruit trees), and slow turfgrass growth rate to reduce mowing frequency.

There are several different classes of plant growth regulator. Known classes include azoles (such as uniconazole, and paclobutrazol), cyclohexane carboxylates (such as trinexapac-ethyl, and prohexadione-calcium), pyrimidinyl carbinols (such as flurprimidol, and ancymidol), quarternary ammoniums (such as chlormequat-chloride, and mepiquat-chloride), and sulphonyl-amino phenyl-acetamides (such as mefluidide).

Plant growth regulators operate by various modes of action. For example, onium-type plant growth retardants such as chlormequat-chloride and mepiquat-chloride, that possess a positively charged ammonium, phosphonium or sulphonium group, function by blocking the synthesis of gibberellin early in the biosynthetic pathway. Growth retardants comprising a nitrogen-containing heterocycle, such as flurprimidol, paclobutrazol and uniconazole-P, act as inhibitors of monooxygenases that catalyse oxidative steps in gibberellin biosynthesis. Structural mimics of 2-oxoglutaric acid, such as the acylcyclohexanediones trinexapac-ethyl and prohexadione-calcium, interfere with the late steps of gibberellin biosynthesis. Other plant growth regulators, such as mefluidide, inhibit cell division and differentiation.

In some cases, herbicidally active ingredients have been shown to be more effective when mixed with other herbicides compared to when applied individually, and this is referred to as "synergism", since the combination demonstrates a potency or activity level exceeding that which it would be expected to have based on knowledge of the individual potencies of the components.

The present invention resides in the discovery that herbicides exhibit an improved herbicidal effect when applied in combination with plant growth regulators. In particular, it has been found that such mixtures have a synergistic effect, providing quicker, better and longer-lasting herbicidal activity than the person skilled in the art would expect given the activity of each active ingredient when applied alone.

According to the present invention, there is provided a method for controlling weeds, comprising applying to the weeds or to the locus where the weeds are present, a mixture of one or more non-selective herbicides and one or more plant growth regulators in a synergistically effective amount, or a composition comprising said mixture(s). Suitably the mixture will comprise at least one non-selective herbicide and at least one plant growth regulator.

The composition contains a herbicidally effective combination of a non-selective herbicide and a plant growth regulator. The term 'herbicide' as used herein denotes a compound which controls or modifies the growth of plants. The term 'non-selective' refers to the spectrum of plant species against which the herbicide is active, non-selective herbicides being active against all plant species. In the context of the present invention, it includes both herbicides that provide total vegetative control, and also herbicides that have a very broad spectrum of activity such as PPO inhibiting herbicides. The term 'synergistically effective amount' indicates the quantity of such compounds which is capable of producing a controlling or modifying effect on the growth of plants, where said effect is greater than the sum of the effects obtained by applying each of the compounds individually. Controlling or modifying effects include all deviation from natural development, for example: killing, retardation, suppression, leaf burn, albinism, dwarfing and the like. For example, plants that are not killed are often stunted and non-competitive with flowering disrupted. The term 'plants' refers to all physical parts of a plant, including seeds, seedlings, saplings, roots, tubers, stems, stalks, foliage and fruits.

Suitably the herbicide is a non-selective herbicide. Suitably, the herbicide belongs to a class selected from the group consisting of PS-I inhibitors, EPSPS inhibitors, glutamine synthetase inhibitors and PPO inhibitors.

In one embodiment of the present invention, the herbicide is a PS-I inhibitor. Such herbicides inhibit photosystem I. Suitably, the PS-I inhibitor is diquat or paraquat.

In one embodiment of the present invention, the herbicide is an inhibitor of EPSPS. Such herbicides inhibit the enzyme 5-enolpyruvateshikimate-3-phosphate-synthase, and consequently disrupt amino acid synthesis. Suitably the EPSPS inhibitor is glyphosate. As used herein, the term glyphosate includes agriculturally acceptable salts or esters thereof.

In one embodiment of the present invention, the herbicide is an inhibitor of glutamine synthetase. Suitably, the herbicide is selected from the group consisting of glufosinate-ammonium and bialaphos (bilanaphos).

In one embodiment of the present invention, the herbicide is a PPO inhibitor. Such herbicides inhibit the protoporphyrinogen IX oxidase, to disrupt cell membranes. The herbicide may be selected from one of the following classes: diphenylether, phenylpyrazole, N-phenylphthalimide, thiadiazole, oxadiazole, triazolinone, oxazolidinedione and pyrimidindione. For example the herbicide may be acifluorfen-Na, bifenox, chlomethoxyfen, fluoroglycofen-ethyl, fomesafen, halosafen, lactofen, oxyfluorfen, fluazolate, pyraflufen-ethyl, cinidon-ethyl, flumioxazin, flumiclorac-pentyl, fluthiacet-methyl, thidiazimin, oxadiazon, oxadiargyl, azafenidin, carfentrazone-ethyl, sulfentrazone, pentoxazone, benzfendizone, butafenacil, saflufenacil, pyraclonil, profluazol or flufenpyr-ethyl. Suitably, the PPO inhibitor is selected from the group consisting of sulfentrazone, oxyfluorfen, lactofen, oxadiazon, fomesafen, saflufenacil, and butafenacil. Suitably, the PPO inhibitor is fomesafen. Suitably, the PPO inhibitor is saflufenacil.

The present invention includes all herbicidally active forms of the above compounds, such as salts, chelates and esters.

Any plant growth regulator may be used in accordance with the present invention. In one embodiment, the plant growth regulator is selected from the group consisting of trinexapac-ethyl, prohexadione-calcium, paclobutrazol, uniconazole, mepiquat-chloride and chlormequat-chloride.

Suitably, the plant growth regulator is a gibberellin biosynthesis inhibitor. Suitably, the plant growth regulator is a class A gibberellin biosynthesis inhibitor. Suitably, the plant growth regulator is a class B gibberellin biosynthesis inhibitor. In a preferred embodiment the plant growth regulator is trinexapac-ethyl, prohexadione-calcium or chlormequat-chloride. Suitably, the plant growth regulator is trinexapac-ethyl. Suitably, the plant growth regulator is prohexadione-calcium. Suitably, the plant growth regulator is chlormequat-chloride.

In accordance with the present invention, there may be mentioned mixtures comprising a non-selective herbicide and trinexapac-ethyl, or compositions comprising the same. Suitably, the mixture for use in the present invention comprises trinexapac-ethyl and a PS-I inhibitor. Suitably, the mixture for use in the present invention comprises trinexapac-ethyl and a EPSPS inhibitor. Suitably, the mixture for use in the present invention comprises trinexapac-ethyl and a glutamine synthetase inhibitor. Suitably, the mixture for use in the present invention comprises trinexapac-ethyl and a PPO inhibitor. Suitably, the mixture for use in the present invention comprises trinexapac-ethyl in admixture with one or more herbicides selected from the group consisting of glyphosate, glufosinate, diquat and paraquat.

The present invention may be used to control a large number of agronomically important weeds, including monocotyledonous weeds and dicotyledonous weeds.

For example, the invention may be used to control dicotyledonous weeds such as *Abutilon* spp., *Ambrosia* spp., *Amaranthus* spp., *Chenopodium* spp., *Euphorbia* spp., *Galium* spp., *Ipomoea* spp., *Polygonum* spp., *Sida* spp., *Sinapis* spp., *Solanum* spp., *Stellaria* spp., *Taraxacum* spp., *Trifolium* spp., *Veronica* spp., *Viola* spp. and *Xanthium* spp.

The invention may also be used to control monocotyledonous weeds such as *Agrostis* spp., *Alopecurus* spp., *Apera* spp., *Avena* spp., *Brachiaria* spp., *Bromus* spp., *Digitaria* spp., *Echinochloa* spp., *Eleusine* spp., *Eriochloa* spp., *Leptochloa* spp., *Lolium* spp., *Ottochloa* spp., *Panicum* spp., *Paspalum* spp., *Phalaris* spp., *Poa* spp., *Rottboellia* spp., *Setaria* spp., *Sorghum* spp., both intrinsically sensitive as well as resistant (e.g. ACCase and/or ALS resistant) biotypes of any of these grass weeds, as well as broadleaf monocotyledonous weeds such as *Commelina* spp., *Monochoria* spp., *Sagittaria* spp. and sedges such as *Cyperus* spp. and *Scirpus* spp.

Suitably, the present invention is used to control monocot weeds, more suitably grasses. In particular, the present invention is used to control annual bluegrass (*Poa annua*), perennial ryegrass (*Lolium perenne*), wild oat (*Avena fatua*), downy brome (*Bromus tectorum*), shattercane (*Sorghum bicolor*), and/or yellow nutsedge (*Cyperus esculentus*).

In one embodiment of the present invention, the mixture comprises trinexapac-ethyl and glyphosate in a synergistically effective amount. Suitably, said mixture is used for the control of dicotyledonous weeds.

In a further embodiment of the present invention, the mixture comprises trinexapac-ethyl and paraquat in a synergistically effective amount. Suitably, said mixture is used for the control of grass weeds.

In a further embodiment of the present invention, the mixture comprises trinexapac-ethyl and glufosinate in a synergistically effective amount. Suitably, said mixture is used for the control of warm season grass weeds.

In a further embodiment of the present invention, the mixture comprises trinexapac-ethyl and fomesafen in a synergistically effective amount. Suitably, said mixture is used for the control of dicot and monocot weeds. More suitably, said mixture is used for the control of grass weeds.

For the purposes of the present invention, the term 'weeds' includes undesirable crop species such as volunteer crops, both conventional and genetically altered, either by means of mutation or transgenic approaches. For example, in the context of turf grass crops such as on a golf course, creeping bentgrass putting green turf can be considered a 'volunteer' if found in a fairway section where a different variety of grass is being cultivated. The other grasses listed below can, similarly, be considered weeds when found in the wrong place.

The 'locus' is intended to include soil, seeds, and seedlings as well as established vegetation.

According to the present invention, there is provided a herbicidal composition comprising at least one non-selective herbicide and at least one plant growth regulator in a synergistically effective amount. In one embodiment, the herbicide belongs to a class selected from the group consisting of PS-I inhibitors, EPSPS inhibitors, glutamine synthetase inhibitors and PPO inhibitors.

Suitably the non-selective herbicide in the herbicidal composition is selected from the group consisting of glyphosate, glufosinate, paraquat and fomesafen.

Suitably the plant growth regulator in the herbicidal composition is selected from the group consisting of trinexapac-ethyl, prohexadione-calcium, paclobutrazol, uniconazole, mepiquat-chloride and chlormequat-chloride. Suitably the plant growth regulator is trinexapac-ethyl, prohexadione-calcium or chlormequat-chloride.

Suitably the herbicidal composition of the present invention comprises trinexapac-ethyl and glyphosate in a synergistically effective amount. Suitably the herbicidal composition of the present invention comprises trinexapac-ethyl and paraquat in a synergistically effective amount. Suitably the herbicidal composition of the present invention comprises trinexapac-ethyl and glufosinate in a synergistically effective amount. Suitably the herbicidal composition of the present invention comprises trinexapac-ethyl and fomesafen in a synergistically effective amount.

In the compositions of this invention, the mixture ratio of herbicide to plant growth regulator at which the herbicidal effect is synergistic lies within the range of between about 1:1000 and about 1000:1. Suitably, the mixture ratio of herbicide to plant growth regulator is between about 1:100 and about 100:1. More suitably, the mixture ratio of herbicide to plant growth regulator is between about 1:1 and about 1:10. For example, where the herbicide is mesotrione and the plant growth regulator is trinexapac-ethyl, a mixture ratio of between about 1:3 and about 1:6 is preferred.

The rate at which the composition of the invention is applied will depend upon the particular type of weed to be controlled, the degree of control required and the timing and method of application. In general, the compositions of the invention can be applied at an application rate of from 0.001 kilograms active ingredient/hectare (kg ai/ha) to about 5.0 kg ai/ha, based on the total amount of active ingredient (mesotrione and trinexapac-ethyl) in the composition. An application rate of from about 0.01 kg ai/ha to about 5.0 kg ai/ha is preferred, with an application rate of from about 0.05 kg ai/ha to 1.0 kg ai/ha being especially preferred. It is noted that the rates used in the examples below are glasshouse rates and are lower than those normally applied in the field as herbicide effects tend to be magnified in such conditions.

In a further aspect, the present invention provides a method of controlling or modifying the growth of weeds comprising applying to the locus of such weeds a herbicidally effective amount of a composition of the invention.

The benefits of the present invention are seen most when the herbicidal composition is applied to control weeds in growing crops of useful plants: such as maize (including field corn, pop corn and sweet corn), cotton, winter and spring cereals (including wheat, barley, rye, oats), rice, potato, sugar/fodder beet, winter and spring rape, leguminous crops (including soybeans), grain sorghum, plantation crops (including bananas, fruit trees, oilpalm, rubber, tree nurseries, vines), sugarcane, vegetables (including asparagus, rhubarb, tomato), sunflower, various berries, flax, cool and warm season turf grasses, and others.

Cool season turfgrasses include, for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annua* L.); bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (*Festuca* L.), such as tall fescue (*Festuca arundinacea* Schreb.), meadow fescue (*Festuca elatior* L.) and fine fescues such as creeping red fescue (*Festuca rubra* L.), chewings fescue (*Festuca rubra* var. commutata Gaud.), sheep fescue (*Festuca ovina* L.) and hard fescue (*Festuca longifolia*); and ryegrasses (*Lolium* L.), such as perennial ryegrass (*Lolium perenne* L.) and annual (Italian) ryegrass (*Lolium multiflorum* Lam.).

Warm season turfgrasses include, for example, Bermudagrasses (*Cynodon* L. C. Rich), including hybrid and common Bermudagrass; Zoysiagrasses (*Zoysia* Willd.), St. Augustinegrass (*Stenotaphrum secundatum* (Walt.) Kuntze); and centipedegrass (*Eremochloa ophiuroides* (Munro.) Hack.).

In addition 'crops' are to be understood to include those crops that have been made tolerant to pests and pesticides, including herbicides or classes of herbicides (and, suitably, the herbicides of the present invention), as a result of conventional methods of breeding or genetic engineering. Tolerance to herbicides means a reduced susceptibility to damage caused by a particular herbicide compared to conventional crop breeds. Crops can be modified or bred so as to be tolerant, for example to EPSPS inhibitors such as glyphosate, or to glufosinate.

The composition of the present invention is useful in controlling the growth of undesirable vegetation by pre-emergence or post-emergence application to the locus where control is desired, depending on the crop over which the combination is applied. In one embodiment, therefore, the herbicidal composition of the invention is applied as a pre-emergent application. In a further embodiment, the herbicidal composition of the invention is applied as a post-emergent application.

The compounds of the invention may be applied either simultaneously or sequentially. If administered sequentially, the components may be administered in any order in a suitable timescale, for example, with up to a week between the time of administering the first component and the time of administering the last component. Suitably, the components are administered within 24 hours. More suitably, the components are administered within a few hours. Suitably, the components are administered within one hour. Suitably, if administered sequentially, the plant growth regulator is applied first. If the components are administered simultaneously, they may be administered separately or as a tank mix or as a pre-formulated mixture of all the components or as a pre-formulated mixture of some of the components tank mixed with the remaining components. In one embodiment the mixture or composition of the present invention may be applied to a crop as a seed treatment prior to planting.

In practice, the compositions of the invention are applied as a formulation containing the various adjuvants and carriers known to or used in the industry. The compositions of the invention may thus be formulated as granules, as wettable powders, as emulsifiable concentrates, as powders or dusts, as flowables, as solutions, as suspensions or emulsions, or as controlled release forms such as microcapsules. These formulations may contain as little as about 0.5% to as much as about 95% or more by weight of active ingredient. The optimum amount for any given compound will depend on formulation, application equipment and nature of the plants to be controlled.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles and are usually applied without dilution to the area in which suppression of vegetation is desired. Typical carriers for granular formulations include fertiliser, sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Particularly suitable is a fertiliser granule carrier. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins. The granular substrate material can be one of the typical carriers mentioned above and/or can be a fertiliser material e.g. urea/formaldehyde fertilisers, ammonium, liquid nitrogen, urea, potassium chloride, ammonium compounds, phosphorus compounds, sulphur, similar plant nutrients and micronutrients and mixtures or combinations thereof. The herbicide and the plant growth regulator may be homogeneously distributed throughout the granule or may be spray impregnated or absorbed onto the granule substrate after the granules are formed.

Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell o membrane materials include natural and synthetic rubbers, cellulosic materials, styrene-butadiene copolymers, polyacrylonitriles, polyacrylates, polyesters, polyamides, polyureas, polyurethanes and starch xanthates.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule and may include solvent in addition to the active compound.

Other useful formulations for herbicidal applications include simple solutions of the active ingredients in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Many of the formulations described above include wetting, dispersing or emulsifying agents. Examples are alkyl and alkylaryl sulphonates and sulphates and their salts, polyhydric alcohols; polyethoxylated alcohols, esters and fatty amines. These agents, when used, normally comprise from 0.1% to 15% by weight of the formulation.

Suitable agricultural adjuvants and carriers, either formulated together and/or added separately, that are useful in formulating the compositions of the invention in the formulation types described above are well known to those skilled in the art. Suitable examples of the different classes are found in the non-limiting list below.

Liquid carriers that can be employed include water, toluene, xylene, petroleum naphtha, crop oils, AMS; acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc. ethylene glycol, propylene glycol, glycerine, N-methyl-2-pyrrolidinone, and the like. Water is generally the carrier of choice for the dilution of concentrates.

Suitable solid carriers include talc, titanium dioxide, pyrophyllite clay, silica, attapulgite clay, kieselguhr, chalk, diatomaxeous earth, lime, calcium carbonate, bentonite clay, fuller's earth, fertiliser, cotton seed hulls, wheat flour, soybean flour, pumice, wood flour, walnut shell flour, lignin and the like.

A broad range of surface-active agents are advantageously employed in both said liquid and solid compositions, especially those designed to be diluted with carrier before application. The surface-active agents can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants, sticking agents, and the like. The compositions can also be formulated with liquid fertilizers or solid, particulate fertiliser carriers such as ammonium nitrate, urea and the like.

An important factor in influencing the usefulness of a given mixture of a herbicide and a plant growth regulator is its tolerance towards crops ("phytotoxicity"). In most cases, this will be determined by the choice of herbicide. In some cases, a beneficial crop is susceptible to the effects of the herbicide. To be effective, an herbicide must cause minimal damage (preferably no damage) to the beneficial crop while maximizing damage to weed species which infest the locus of the crop. To preserve the beneficial aspects of herbicide use and to minimize crop damage, it is known to apply herbicides in combination with an antidote/safener, if necessary. As used here in 'antidote' describes a compound which has the safening effect of establishing herbicide selectivity, i.e. continued herbicidal phytotoxicity to weed species by the herbicide and reduced or non-phytotoxicity to the cultivated crop species. The term 'antidotally effective amount' describes an amount of an antidote compound which counteracts to some degree a phytotoxic response of a beneficial crop to an herbicide. If necessary or desired for a particular application or crop, the composition of the present invention may contain an antidotally effective amount of an antidote for the herbicides of the invention. Those skilled in the art will be familiar with antidotes which are suitable for use with particular herbicides and plant growth regulators and can readily determine an antidotally effective amount for a particular mixture. In one embodiment, the present invention is used to control weeds in crops that are resistant to the herbicide, so that a safener is not required.

Suitably the present invention is used to control weeds in crops that are resistant to the herbicidal mixture or composition. For example, it may be used to control weeds in glyphosate tolerant corn. In one embodiment of the present invention, there is provided a method for controlling weeds in a crop, comprising applying to the crop a herbicidal composition comprising a non-selective herbicide and a plant growth regulator in a synergistically effective amount, wherein the crop is resistant to the non-selective herbicide.

In addition, further, other biocidally active ingredients or compositions may be combined with the herbicidal composition of this invention. For example, the compositions may contain, in addition to the herbicide and plant growth regulator, other herbicides, insecticides, fungicides, bactericides, acaracides, nematicides and/or plant growth regulators, in order to broaden the spectrum of activity.

Each of the above formulations can be prepared as a package containing the herbicides together with other ingredients of the formulation (diluents, emulsifiers, surfactants, etc.). The formulations can also be prepared by a tank mix method, in which the ingredients are obtained separately and combined at the grower site.

These formulations can be applied to the areas where control is desired by conventional methods. Dust and liquid compositions, for example, can be applied by the use of powerdusters, broom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as disking, dragging or mixing operations.

The present invention can be used in any situation in which weed control is desired, for example in agriculture, on golf courses, or in gardens.

The following examples are for illustrative purposes only. The examples are not intended as necessarily representative of the overall testing performed and are not intended to limit the invention in any way. As one skilled in the art is aware, in herbicidal testing, a significant number of factors that are not readily controllable can affect the results of individual tests and render them non-reproducible. For example, the results may vary depending on environmental factors, such as amount of sunlight and water, soil type, pH of the soil, temperature and humidity, among others. Also, the depth of planting, the application rate of individual and combined herbicides, the application rate of any antidote, and the ratio of the individual herbicides to one another and/or to an antidote as well as the nature of crops or weeds being tested can affect the results of the test. Results may vary from crop to crop within the crop varieties.

EXAMPLES

In the following tests, herbicides were applied at reduced field rates because herbicide effects are magnified in a glasshouse environment. The rates tested were selected to give between about 50 and 70% control with herbicides applied alone, so that any synergistic effect could be readily detected when testing mixtures.

Example 1

Control of Barnyard Grass with Mesotrione and Trinexapac-Ethyl Applied Post-Emergence A glasshouse trial was carried out. Barnyard grass seeds were sown into standard glasshouse potting mix (1:1 v/v Promix:Vero sand soil) contained in 10 cm square plastic pots. Treatments were replicated three times. Mesotrione (in the form Callisto® 480SE) (MST) was applied post-emergence to barnyard grass (*Echinochloa crus-galli*) at either 12.5 g ai/ha or 25 g ai/ha with or without trinexapac-ethyl (in the form of Palisade®) (TXP). When used, trinexapac-ethyl was applied at a rate of 200 g ai/ha or 400 g ai/ha. The adjuvant system was X-77 at 0.1% v/v in deionised water. 200 liters of herbicide/adjuvant system was used per hectare. General weed control was evaluated at 6-9 and 14-18 days after treatment (DAT). It is noted that all herbicides were applied at reduced field rates because herbicide effects are magnified in a glasshouse environment. Rates were chosen to give a 50 to 70% level of control with herbicides applied alone as this allows for detection of any synergistic effect when tank mixtures are used.

Table 1 shows the results, as evaluated using the Colby formula. The expected result for (Y+Z) is (Y+Z)−(Y×Z/100) where Y and Z are the 'observed' results for Y and Z on their own. Control from the tank mixture is synergistic if the actual result is significantly higher than the expected result (significance based on Student-Newman-Keuls multiple range test).

TABLE 1

| | Rate (g ai/ha) | MST at 12.5 g ai/ha | | MST at 25 g ai/ha | |
|---|---|---|---|---|---|
| | | A | E | A | E |
| TXP | 200 | 38* | 7 | 40* | 25 |
| TXP | 400 | 47* | 25 | 57* | 40 |

A = actual weed control value; E = expected weed control value (calculated using the Colby formula);
*= synergy Using the Colby formula and Student-Newman-Keuls multiple range test, synergy was seen at both the high and low rates of mesotrione and the low and high rates of trinexapac-ethyl when a combination of trinexapac-ethyl and mesotrione was used to control barnyard grass.

Example 2

Control of Giant Foxtail with Mesotrione and Trinexapac-Ethyl Applied Post-Emergence A glasshouse trial was carried out as described in Example 1, substituting barnyard grass for *Setaria faberi* (giant foxtail). The rates used, and results obtained, are indicated in Table 2 below.

TABLE 2

| Rate (g ai/ha) | MST at 25 g ai/ha | | MST at 50 g ai/ha | | MST at 100 g ai/ha | | MST at 200 g ai/ha | |
|---|---|---|---|---|---|---|---|---|
| | A | E | A | E | A | E | A | E |
| TXP 200 | 35.0* | 32.5 | 32.5 | 32.5 | 35.0* | 32.5 | 46.3* | 32.5 |
| TXP 400 | 36.3 | 45.0 | 45.0 | 54.0 | 48.8* | 45.0 | 55.0* | 45.0 |
| TXP 800 | 51.3* | 43.8 | 43.8 | 43.8 | 53.8* | 43.8 | 58.8* | 43.8 |

A = actual weed control value; E = expected weed control value (calculated using the Colby formula);
* = synergy Synergy in control of giant foxtail was seen at many of the rate combinations tested, but especially for high rates of mesotrione in combination with all rates of trinexapac-ethyl tested.

Example 3

Control of Large Crabgrass with Mesotrione and Trinexapac-Ethyl Applied Post-Emergence A glasshouse trial was carried out as described in Example 1, substituting barnyard grass for *Digitaria sanguinalis* (large crabgrass). The rates used, and results obtained, are indicated in Table 3 below.

TABLE 3

| Rate (g ai/ha) | MST at 25 g ai/ha | | MST at 50 g ai/ha | | MST at 100 g ai/ha | | MST at 200 g ai/ha | |
|---|---|---|---|---|---|---|---|---|
| | A | E | A | E | A | E | A | E |
| TXP 200 | 52.5* | 24.9 | 73.8* | 44.5 | 77.0* | 55.0 | 87.5* | 68.4 |
| TXP 400 | 45.0* | 30.0 | 60.0* | 48.3 | 75.8* | 58.0 | 93.3* | 70.5 |
| TXP 800 | 60.0* | 47.2 | 72.5* | 61.0 | 81.3* | 68.3 | 91.3* | 77.8 |

A = actual weed control value; E = expected weed control value (calculated using the Colby formula);
* = synergy Synergy in control of large crabgrass was seen at all rate combinations tested.

Example 4

Control of Fall Panicum with Mesotrione and Trinexapac-Ethyl Applied Post-Emergence A glasshouse trial was carried out as described in Example 1, substituting barnyard grass for *Panicum dichotomiflorum* (fall *panicum*). The rates used, and results obtained, are indicated in Table 4 below.

TABLE 4

| Rate (g ai/ha) | MST at 25 g ai/ha | | MST at 50 g ai/ha | | MST at 100 g ai/ha | | MST at 200 g ai/ha | |
|---|---|---|---|---|---|---|---|---|
| | A | E | A | E | A | E | A | E |
| TXP 200 | 27.5 | 36.5 | 23.8 | 38.2 | 36.3 | 41.6 | 58.8* | 53.6 |
| TXP 400 | 38.8* | 32.9 | 40.0* | 34.8 | 47.5* | 38.4 | 62.5* | 51.1 |
| TXP 800 | 43.8* | 36.5 | 37.5 | 38.2 | 46.3* | 41.6 | 68.8* | 53.6 |

A = actual weed control value; E = expected weed control value (calculated using the Colby formula);
* = synergy Synergy in control of fall *panicum* was seen at many of the rate combinations tested, but especially for high rates of mesotrione in combination with all rates of trinexapac-ethyl tested.

Example 5

Control of Goosegrass with Mesotrione and Trinexapac-Ethyl Applied Post-Emergence A glasshouse trial was carried out as described in Example 1, substituting barnyard grass for *Eleusine indica* (goosegrass). The rates used, and results obtained, are indicated in Table 5 below.

TABLE 5

| Rate (g ai/ha) | MST at 25 g ai/ha | | MST at 50 g ai/ha | | MST at 100 g ai/ha | | MST at 200 g ai/ha | |
|---|---|---|---|---|---|---|---|---|
| | A | E | A | E | A | E | A | E |
| TXP 200 | 53.8* | 39.7 | 62.5* | 44.9 | 71.3* | 44.9 | 83.8* | 47.5 |
| TXP 400 | 57.5* | 50.4 | 64.5* | 54.7 | 76.3* | 54.7 | 85.0* | 56.9 |
| TXP 800 | 60.0* | 56.9 | 65.0* | 60.7 | 73.8* | 60.7 | 90.0* | 62.5 |

A = actual weed control value; E = expected weed control value (calculated using the Colby formula);
* = synergy Synergy in control of goosegrass was seen at all rate combinations tested.

Example 6

Weed Control with Mixtures of Non-Selective Herbicides and Trinexapac-Ethyl Applied Post-Emergence A glasshouse trial was carried out to test the activity of various herbicides (each at 2 different rates) in combination with trinexapac-ethyl (at 3 different rates) against a variety of weed species. The dicot weeds tested were SINAR (*Sinapis arvensis*, wild mustard), CHEAL (*Chenopodium album*, common lambsquarter), IPOHE (*Ipomoea hederacea*, ivyleaf morningglory) and XANST (*Xanthium strumarium*, common cocklebur). The monocot weeds tested were POANN (*Poa annua*, annual bluegrass), LOLPE (*Lolium perenne*, perennial ryegrass), AVEFA (*Avena fatua*, wild oat), BROTE (*Bromus tectorum*, downy brome), SORVU (*Sorghum bicolor*, shattercane) and CYPES (*Cyperus esculentus*, yellow nutsedge).

Seeds of each species were sown in standard potting mix in 50 cm plastic troughs. All compounds were applied as standard commercial formulations (Touchdown IQ® diammonium salt (SL360), Gramoxone Extra® (SL100), Basta® (SL200), Flex® (SL240), Moddus® (EC250)) at rates as listed in the table below. The adjuvant system was X-77 at 0.1% v/v in deionised water. 500 liters of herbicide/adjuvant system was used per hectare. General weed control was evaluated at 14 days after treatment (DAT). It is noted that all herbicides were applied at reduced field rates because herbicide effects are magnified in a glasshouse environment. Rates were chosen to give a 50 to 70% level of control with herbicides applied alone as this allows for detection of any synergistic effect when tank mixtures are used.

Tables 6 (dicot weeds), 7 (monocot weeds, cool season) and 8 (monocot weeds, warm season) shows the results, as evaluated using the Colby formula. The expected result for (Y+Z) is (Y+Z)−(Y×Z/100) where Y and Z are the 'observed' results for Y and Z on their own. Control from the tank mixture is synergistic if the actual result is significantly higher than the expected result (significance based on Student-Newman-Keuls multiple range test).

TABLE 6 dicot weeds

| Treatment (rates are in g ai/ha) | SINAR A | SINAR E | CHEAL A | CHEAL E | IPOHE A | IPOHE E | XANST A | XANST E |
|---|---|---|---|---|---|---|---|---|
| Glyphosate + Trinexapac (50 + 50 g) | 70 | n/a | 0 | 0 | 30* | 0 | 10** | 40 |
| Glyphosate + Trinexapac (100 + 50 g) | 70 | n/a | 0 | 0 | 0 | 0 | 40 | 50 |
| Glyphosate + Trinexapac (50 + 100 g) | 50 | 40 | 0 | 0 | 30* | 0 | 40** | 60 |
| Glyphosate + Trinexapac (100 + 100 g) | 70* | 40 | 0 | 0 | 30* | 0 | 40 | 30 |
| Glyphosate + Trinexapac (50 + 200 g) | 60* | 40 | 0 | 0 | 20* | 0 | 20 | 30 |
| Glyphosate + Trinexapac (100 + 200 g) | 70* | 40 | 0 | 0 | 70* | 0 | 50 | 60 |
| Paraquat + Trinexapac (50 + 50 g) | 80 | 80 | 40 | 40 | 60* | 40 | 90* | 70 |
| Paraquat + Trinexapac (100 + 50 g) | 80 | 80 | 90* | 70 | 100 | 100 | 100 | 90 |
| Paraquat + Trinexapac (50 + 100 g) | 70 | 70 | 80 | n/a | 30 | 40 | 90* | 70 |
| Paraquat + Trinexapac (100 + 100 g) | 70 | 80 | 70 | 70 | 70** | 100 | 80* | 50 |
| Paraquat + Trinexapac (50 + 200 g) | 40** | 70 | 70 | n/a | 30 | 40 | 90* | 60 |
| Paraquat + Trinexapac (100 + 200 g) | 40** | 80 | 90* | 70 | 30** | 100 | 100 | 90 |
| Glufosinate + Trinexapac (50 + 50 g) | 50 | 50 | 0 | 0 | 0 | 0 | 70* | 50 |
| Glufosinate + Trinexapac (100 + 50 g) | 60 | 60 | 0 | 0 | 0 | 0 | 70 | 60 |
| Glufosinate + Trinexapac (50 + 100 g) | 20** | 40 | M | n/a | 20* | 0 | 90 | 90 |
| Glufosinate + Trinexapac (100 + 100 g) | 80** | 100 | 0 | 0 | 20* | 0 | 90* | 70 |
| Glufosinate + Trinexapac (50 + 200 g) | 40 | 40 | 0 | n/a | 30* | 0 | 80* | 50 |
| Glufosinate + Trinexapac (100 + 200 g) | 80** | 100 | 0 | 0 | 70* | 0 | 70* | 40 |
| Fomesafen + Trinexapac (10 + 50 g) | 70 | 70 | 100 | 100 | 80* | 40 | 60 | 60 |
| Fomesafen + Trinexapac (40 + 50 g) | 100 | 100 | 100* | 80 | 80 | 80 | 70* | 40 |
| Fomesafen + Trinexapac (10 + 100 g) | 80 | 90 | M | n/a | 60* | 40 | 40 | 40 |
| Fomesafen + Trinexapac (40 + 100 g) | 100 | 100 | 100* | 80 | 70 | 80 | 10 | 10 |
| Fomesafen + Trinexapac (10 + 200 g) | 80 | 90 | 60 | n/a | 90* | 40 | 70 | 60 |
| Fomesafen + Trinexapac (40 + 200 g) | 80** | 100 | 100* | 80 | 60** | 80 | 100* | 60 |

A = actual % control observed; E = expected % control (as calculated using Colby formula); M = missing datapoint; n/a = Colby calculation not possible due to missing datapoint;
*= significant synergy;
**= significant antagonism

TABLE 7 monocot weeds, cool season

| Treatment (rates are in g ai/ha) | POAAN A | POAAN E | LOLPE A | LOLPE E | AVEFA A | AVEFA E | BROTE A | BROTE E |
|---|---|---|---|---|---|---|---|---|
| Glyphosate + Trinexapac (50 + 50 g) | 0 | 0 | 0 | 0 | 0 | 0 | 0 | 0 |
| Glyphosate + Trinexapac (100 + 50 g) | 0 | 0 | 0 | 0 | 0 | 0 | 0 | 0 |
| Glyphosate + Trinexapac (50 + 100 g) | 30* | 0 | 0 | 0 | 0 | 0 | 0 | 0 |
| Glyphosate + Trinexapac (100 + 100 g) | 30* | 0 | 0 | 0 | 0 | 0 | 0 | 0 |
| Glyphosate + Trinexapac (50 + 200 g) | 0 | 0 | 0 | 0 | 0 | 0 | 0 | 0 |
| Glyphosate + Trinexapac (100 + 200 g) | 0 | 0 | 30* | 0 | 0 | 0 | 0 | 0 |
| Paraquat + Trinexapac (50 + 50 g) | 0 | 10 | 0 | 10 | 0 | 0 | 50 | 40 |
| Paraquat + Trinexapac (100 + 50 g) | 20** | 40 | 60 | 70 | 0** | 20 | 70 | 60 |
| Paraquat + Trinexapac (50 + 100 g) | 10 | 10 | 40* | 10 | 0 | 0 | 60* | 40 |
| Paraquat + Trinexapac (100 + 100 g) | 10** | 40 | 70 | 70 | 40* | 20 | 70 | 60 |
| Paraquat + Trinexapac (50 + 200 g) | 30* | 10 | 30* | 10 | 30* | 0 | 60* | 40 |
| Paraquat + Trinexapac (100 + 200 g) | 70* | 40 | 70 | 70 | 60* | 20 | 70 | 60 |
| Glufosinate + Trinexapac (50 + 50 g) | 0 | 0 | 0 | 0 | 0 | 0 | 0 | 0 |
| Glufosinate + Trinexapac (100 + 50 g) | 0 | 0 | 0 | 0 | 0 | 0 | 0 | 0 |
| Glufosinate + Trinexapac (50 + 100 g) | 0 | 0 | 0 | 0 | 0 | 0 | 0 | 0 |
| Glufosinate + Trinexapac (100 + 100 g) | 0 | 0 | 0 | 0 | 0 | 0 | 0 | 0 |
| Glufosinate + Trinexapac (50 + 200 g) | 0 | 0 | 0 | 0 | 0 | 0 | 0 | 0 |
| Glufosinate + Trinexapac (100 + 200 g) | 20* | 0 | 0 | 0 | 0 | 0 | 0 | 0 |
| Fomesafen + Trinexapac (10 + 50 g) | 0 | 0 | 10 | 0 | 0 | 10 | 40 | 30 |
| Fomesafen + Trinexapac (40 + 50 g) | 20* | 0 | 40* | 0 | 60* | 30 | 60 | 60 |
| Fomesafen + Trinexapac (10 + 100 g) | 0 | 0 | 0 | 0 | 30* | 10 | 60* | 30 |
| Fomesafen + Trinexapac (40 + 100 g) | 10 | 0 | 20* | 0 | 50* | 30 | 70 | 60 |
| Fomesafen + Trinexapac (10 + 200 g) | 30* | 0 | 20* | 0 | 20 | 10 | 60* | 30 |
| Fomesafen + Trinexapac (40 + 200 g) | 50* | 0 | 30* | 0 | 50* | 30 | 70 | 60 |

A = actual % control observed; E = expected % control (as calculated using Colby formula); M = missing datapoint; n/a = Colby calculation not possible due to missing datapoint;
*= significant synergy;
**= significant antagonism

TABLE 8

| monocot weeds, warm season | | | | |
|---|---|---|---|---|
| | SORVU | | CYPES | |
| Treatment (rates are in g ai/ha) | A | E | A | E |
| Glyphosate + Trinexapac (50 + 50 g) | 20 | 20 | 0 | 10 |
| Glyphosate + Trinexapac (100 + 50 g) | 20** | 40 | 20** | 50 |
| Glyphosate + Trinexapac (50 + 100 g) | 30 | 20 | 10* | −10 |
| Glyphosate + Trinexapac (100 + 100 g) | 40 | 40 | 40** | 70 |
| Glyphosate + Trinexapac (50 + 200 g) | 40* | 28 | 20 | 20 |
| Glyphosate + Trinexapac (100 + 200 g) | 40 | 46 | 20** | 40 |
| Paraquat + Trinexapac (50 + 50 g) | 50 | 50 | 20* | 0 |
| Paraquat + Trinexapac (100 + 50 g) | 90 | 100 | 40 | 30 |
| Paraquat + Trinexapac (50 + 100 g) | 50 | 50 | 20* | 0 |
| Paraquat + Trinexapac (100 + 100 g) | 100 | 100 | 60 | 70 |
| Paraquat + Trinexapac (50 + 200 g) | 80* | 55 | 30* | 10 |
| Paraquat + Trinexapac (100 + 200 g) | 80** | 100 | 40 | 30 |
| Glufosinate + Trinexapac (50 + 50 g) | 0 | 0 | 20 | 20 |
| Glufosinate + Trinexapac (100 + 50 g) | 40* | 10 | 10 | 20 |
| Glufosinate + Trinexapac (50 + 100 g) | 40* | 0 | 0* | −20 |
| Glufosinate + Trinexapac (100 + 100 g) | 50* | 10 | 20 | 10 |
| Glufosinate + Trinexapac (50 + 200 g) | 40* | 10 | 30 | 20 |
| Glufosinate + Trinexapac (100 + 200 g) | 70* | 19 | 30 | 40 |
| Fomesafen + Trinexapac (10 + 50 g) | 70* | 50 | 0* | −20 |
| Fomesafen + Trinexapac (40 + 50 g) | 80* | 50 | 30* | −40 |
| Fomesafen + Trinexapac (10 + 100 g) | 70* | 50 | 0 | 0 |
| Fomesafen + Trinexapac (40 + 100 g) | 80* | 50 | 0 | −10 |
| Fomesafen + Trinexapac (10 + 200 g) | 70* | 55 | 10* | −20 |
| Fomesafen + Trinexapac (40 + 200 g) | 80* | 55 | 40* | −60 |

A = actual % control observed; E = expected % control (as calculated using Colby formula);
M = missing datapoint; n/a = Colby calculation not possible due to missing datapoint;
* = significant synergy;
** = significant antagonism Some variation in biological data is inevitable. However, the data clearly demonstrates that synergy is observed when combining non-selective herbicides with trinexapac-ethyl, at various rates and against various different dicot and monocot weed species.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A method for controlling weeds, comprising applying to the weeds or to the locus where the weeds are present, a mixture of at least one non-selective herbicide (A) and at least one plant growth regulator (B) in a synergistically effective amount with a mixture ratio of A:B of from about 1:1 to about 1:10, or a composition comprising said mixture, wherein the plant growth regulator (B) is trinexapac-ethyl and wherein the herbicide (A) is selected from the group consisting of paraquat and fomesafen.

2. The method claim 1, wherein said weeds are monocotyledonous weeds.

3. The method according to claim 1, wherein the herbicide is paraquat.

4. The method claim 3, wherein said weeds are monocotyledonous weeds.

5. The method according to claim 1, wherein the herbicide is fomesafen.

6. The method claim 5, wherein said weeds are monocotyledonous weeds.

7. The method according to claim 1, wherein the mixture is applied post-emergence of the weeds.

8. The method according to claim 1, wherein the composition is applied at an application rate of from about 0.001 kg ai/ha to about 5.0 kg ai/ha.

9. The method according to claim 1, wherein the composition is applied at an application rate of from about 0.01 kg ai/ha to about 5.0 kg ai/ha.

10. The method according to claim 1, wherein the composition is applied at an application rate of from about 0.05 kg ai/ha to about 1.0 kg ai/ha.

11. The method of claim 1, wherein said weeds are *Chenopodium album* L.

12. A method for controlling weeds in a crop, comprising applying to the crop a herbicidal composition comprising a non-selective herbicide (A) and a plant growth regulator (B) in a synergistically effective amount with a mixture ratio of A:B of from about 1:1 to about 1:10, wherein the crop is resistant to the non-selective herbicide, the plant growth regulator (B) is trinexapac-ethyl, and wherein the herbicide (A) is selected from the group consisting of paraquat and fomesafen.

13. The method according to claim 12, wherein the herbicidal composition is applied post-emergence of the weeds.

14. The method according to claim 12, wherein the herbicidal composition is applied at an application rate of from about 0.01 kg ai/ha to about 5.0 kg ai/ha.

15. The method according to claim 12, wherein the herbicidal composition is applied at an application rate of from about 0.05 kg ai/ha to about 1.0 kg ai/ha.

16. The method claim 12, wherein said weeds are monocotyledonous weeds and said herbicide is fomesafen.

17. The method claim 12, wherein said weeds are monocotyledonous weeds and said herbicide is paraquat.

18. The method of claim 17, wherein said monocotyledonous weeds are *Cyperus esculentus* L. or *Bromus tectorum* L.

19. A herbicidal composition comprising at least one non-selective herbicide (A) and at least one plant growth regulator (B) in a synergistically effective amount with a mixture ratio of A:B of from about 1:1 to about 1:10, wherein the plant growth regulator (B) is trinexapac-ethyl and wherein the herbicide (A) is selected from the group consisting of paraquat and fomesafen.

20. The herbicidal composition according to claim 19, wherein the herbicide is paraquat.

21. The herbicidal composition according to claim 19, wherein the herbicide is fomesafen.

* * * * *